United States Patent [19]

Paradis

[11] Patent Number: 5,069,621

[45] Date of Patent: Dec. 3, 1991

[54] DENTAL APPLIANCE

[76] Inventor: Joseph R. Paradis, B212 Mariners Point, Hilton Head Island, S.C. 29926

[21] Appl. No.: 245,004

[22] Filed: Sep. 15, 1988

[51] Int. Cl.$^5$ .............................................. A61C 3/00
[52] U.S. Cl. ................. 433/147; 128/62 A; 132/321
[58] Field of Search ............... 132/321, 328, 329, 309; 433/146, 147, 143, 127; 128/62 A; 15/110, 176.5, 176.6, 176.1, 176.4; 7/167

[56] References Cited

U.S. PATENT DOCUMENTS

| 1,605,320 | 11/1926 | Bates | 433/147 |
| 1,619,212 | 3/1927 | Neederman | 132/309 |
| 3,050,072 | 8/1962 | Diener | 132/321 |
| 3,466,689 | 9/1969 | Aurelio et al. | 128/62 A |
| 3,660,902 | 5/1972 | Axelsson | 132/321 |
| 4,033,007 | 7/1977 | Hadary | 15/176.4 |
| 4,114,216 | 9/1978 | Gatby | 7/167 |
| 4,222,143 | 9/1980 | Tarrson et al. | 132/321 |
| 4,660,583 | 4/1987 | Brown | 132/329 |
| 4,731,896 | 3/1988 | de La Tour | 128/62 A |

Primary Examiner—Cary E. Stone
Attorney, Agent, or Firm—George E. Kersey

[57] ABSTRACT

A dental appliance in which an elongated handle has a rectangular aperture at one end for removably receiving an insert with a rectangular cross section hub that has at least one elongated detent channel which is engageable with a complementary elongated protuberance within the aperture. The channel and protuberance may be perpendicular or parallel with respect to the major axis of the hub insert. The hub is rigid and protrudes from the opposite side of the handle aperture so that the insert may be expelled from the handle by applying pressure to the protrusion. Once removed, the insert may be replaced or readied for reverse installation on the handle, particularly where the portion of the handle containing the aperture is angled.

18 Claims, 2 Drawing Sheets

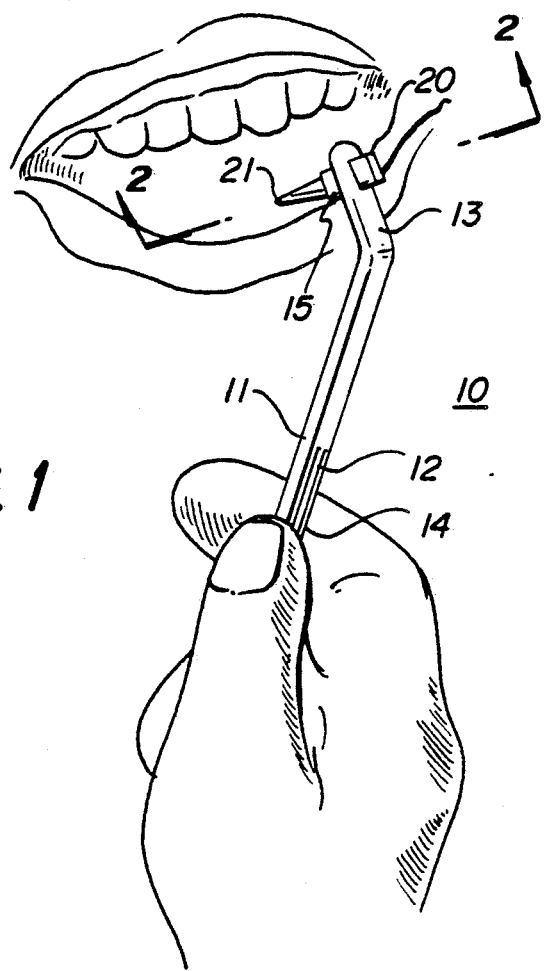
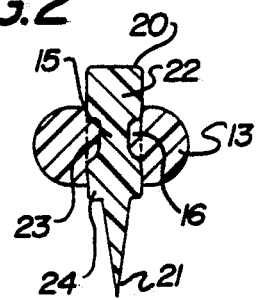
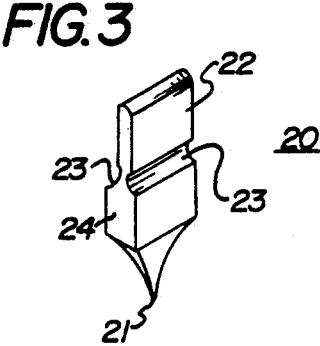
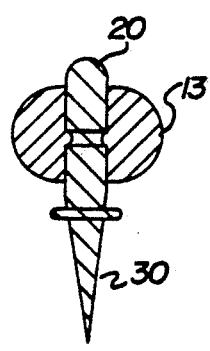
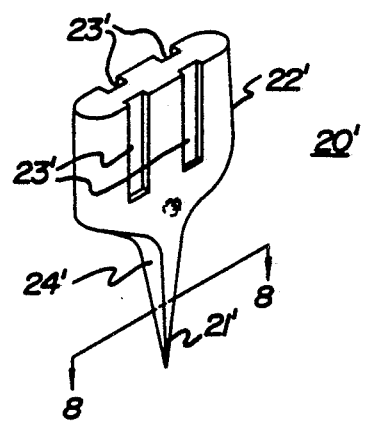

DENTAL APPLIANCE

BACKGROUND OF THE INVENTION

This invention relates to instruments for dental care and more particularly to specialized instruments, including picks and brushes, used to remove plaque, as well as clean root areas and the interproximal spaces between teeth. In addition, to maintain healthy gum tissue, it is desirable to provide for massage. This will develop thicker and healthier gum surface layers.

A number of instruments have been designed for removal of plaque and massaging gum tissue. These instruments have picks and brushes which are applied to gum and tooth surfaces.

It is necessary to provide a handle to firmly hold the pick or brush in place while in use. Additionally, a handle provides for securing the pick or brush. A secure grip allows the pick or brush to be projected perpendicularly from the tip of the handle to facilitate movement in the interproximal spaces and prevent the pick or brush from rotating or bending about its axis.

The requirement for a handle has resulted in a more expensive construction than required for other usages. For example, Burns U.S. Pat. No. 3,559,226 has a metal handle for holding an interproximal implement, with a retention chuck having screw threads and knurling. The construction of such a metal handle involves significant costs. The metal handle also is unsatisfactory in that overtightening can result in a damaged appliance. Conversely under-tightening can also result in damage. While plastic handles are available they are not easily adapted to the type of construction shown in Burns.

When the dental appliance includes a pick it is important to provide a suitable handle to properly position the pick relative to the mouth. If the handle holds a projecting wooden toothpick the opposite end of the toothpick must be severed by breaking. This is likely to result in sharp projecting wooden fibers which can leave splinters.

Other attempts to provide a suitable dental appliance are illustrated by Naylo U.S. Pat. No. 451,293; Uster U.S. Pat. No. 1,291,282; Bixler U.S. Pat. No. 1,397,395; Withycombe U.S. Pat. No. 1,723,226; Eisenberg U.S. Pat. No. 1,784,986; Adams U.S. Pat. No. 2,805,475; Abreneu U.S. Pat. No. 3,430,345; Boone U.S. Pat. No. 3,471,929; Marquis U.S. Pat. No. 3,892,040; Wagner U.S. Pat. No. 4,326,548; Jansbeski U.S. Pat. No. 4,643,676. Illustrative of the continuing objections to prior art devices is U.S. Pat. No. 4,222,143 and cited references in which the handle is required to have a sleeve in order to firmly hold the dental member in place on the member.

Accordingly it is an object of the invention to facilitate the production and use of dental appliances. A related object is to provide a low cost dental appliance which can be produced rapidly and inexpensively.

Another object of the invention is to provide a dental appliance which eliminates the need for threaded chucks and sleeves, while providing a suitable holding capacity for the member held by the handle.

Another object of the invention is to eliminate the danger from splinters associated with the use of wooden picks with dental appliances.

A further object is to provide a dental appliance in which the orientation of the cleansing or massaging implement can be readily changed to accommodate different regions of the mouth.

A related object is to facilitate the change of position for the change of dental implements used for cleaning and massaging gums.

SUMMARY OF THE INVENTION

In accomplishing the foregoing and related objects the invention provides an appliance with opposite end portions and an aperture in one of the portions. A removable insert is positioned in the aperture, which is provided with projections for securing the removable insert.

The removable insert is a dental engagement member used for cleaning and massaging teeth and gums. It may be a dental pick or dental brush.

The removable insert includes a hub with a detent and is insertable into the aperture which extends through the handle. The insert has a major axis that is perpendicular to the detent, which can be a groove, or multiple grooves.

The handle of the appliance can be made of plastic, while the insert may be plastic or cellulosic.

The insert is retained by a projection contained within the aperture of the handle. When the aperture extends through the end portion of the handle, the insert is bidirectionally insertable.

In accordance with another aspect of the invention the handle is fluted with longitudinal grooves which reduce the mass of the handle and facilitates gripping. The end portion of the handle that contains the insert is angled with respect to the remainder of the handle. When the insert projects through the aperture of the handle, this facilitates the removal of and interchange of the insert.

In a method of fabricating a dental appliance in accordance with the invention, a handle is produced with an aperture that contains a projection for removably containing an insert. The insert desirably has a detent for engaging the projection in the aperture of the handle. The inserts can be provided as a clip of selectively detachable members which are individually removed from the remainder of the clip and inserted into the aperture of the handle.

In a method of preparing the dental appliance for use, a contact member or insert is placed at the entrance of the aperture in the handle and the insert is depressed into the aperture of the handle until it makes locking contact with the handle. The insert can be pushed into the aperture until a hub portion protudes beyond an opposite entry. When pressure is applied to the protrusion the insert is readily expelled for replacement or reorientation with respect to the handle.

DESCRIPTION OF THE DRAWINGS

Other aspects of the invention will become apparent after considering several illustrative embodiments, taken in conjunction with the drawings in which:

FIG. 1 is a schematic view illustrating the use of a dental appliance in accordance with the invention;

FIG. 2 is a cross-sectional view taken along the lines 2—2 of FIG. 1 showing the locking engagement of a dental insert within the receiving aperture of a handle;

FIG. 3 is a perspective view of the insert of FIG. 1;

FIG. 4 is a cross-sectional view similar to that of FIG. 2 showing an alternative insert for the handle;

FIGS. 7 and 8 are views of an alternative insert.

DETAILED DESSCRIPTION

Figure 5A:
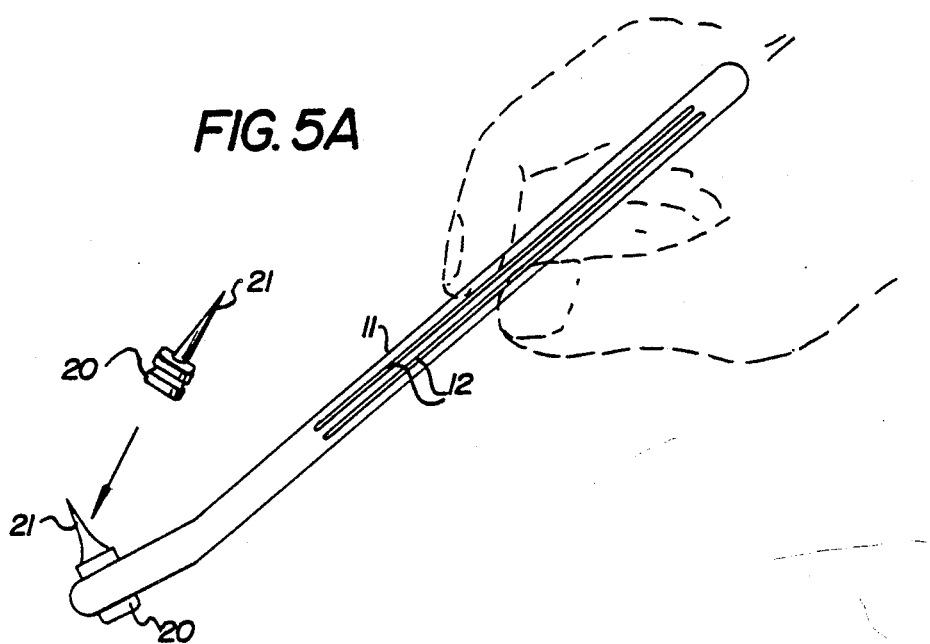
FIG. 5A illustrates the ready removal of an insert pick from a supporting handle.

With reference to the drawings FIG. 1 shows a dental appliance 10 formed by an elongated handle 11 and an insert member 20. As seen in FIG. 1 the handle 11 has longitudinal grooves or flutings 12 which facilitate the gripping of the handle by the hand of a user. In addition the flutings reduce the weight and increase the rigidity of the handle.

As also is seen in FIG. 1 the handle 11 includes an insert portion 13 which forms an angle in relation to the hand held portion 14. Near one end of the insert portion 13 there is an aperture 15 that receives the insert member 20. The angle between the handle portions 13 and 14 facilitate the placement of the insert tip 21 in relation to the teeth and gums of the user.

As indicated in the cross-sectional view of FIG. 2 the insert 20 has a shank 22 with a detent 23 and protruding portion 24. To retain the insert 20 securely within the aperture 15 the holder portion 13 includes projections 16 that are in locking engagement with the recesses 23 of the member 20. While two recesses 23 are shown in FIG. 2 it will be understood that a single recess can be employed and the recesses can take a wide variety of other forms.

Details of the insert 20 are shown in FIG. 3. The tip 21 is proportioned to be suitable for the removal of plaque and interproximal manipulations. The insert may take a wide variety of other forms as illustrated by the brush 30 in FIG. 4.

Figure 5B:
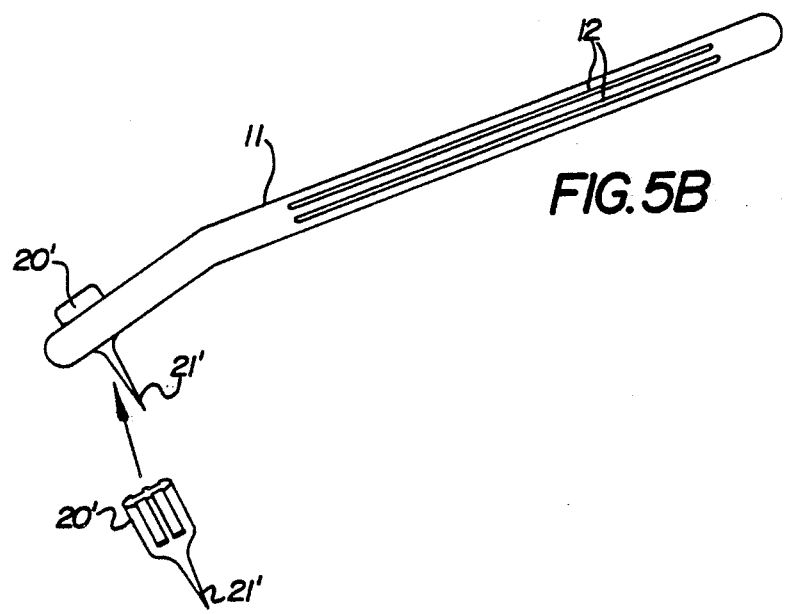
FIG. 5B illustrates the reorientation of the pick of FIG. 5A in the handle.

In addition, because of the locking engagement of the insert with the handle and the extension of the hub 24 beyond the opposite entry of the aperture in the handle, the insert is easily removed as shown in FIG. 5A by pushing the hub against a flat surface. Once the insert is removed, it may be reoriented in relation to the handle by reinserting as shown in FIG. 5B. In addition the insert may be replaced when the tip 21 has worn away or is unsatisfactory because of breakage.

Figure 6:
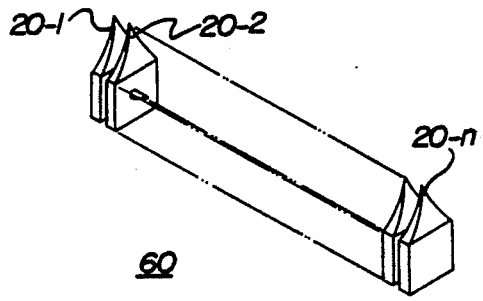
FIG. 6 is a perspective view of a clip of inserts in accordance with the invention.

The handle 11 is desirably produced by injection molding of plastic. Similarly the inserts may be produced by molding and can take the form of a clip 60 as shown in FIG. 6. The clip 60 is constituted by a set of individual members 20-1 through 20-n which are individually removable from the clip 60 and insertable as shown in FIG. 5B or the converse. In addition to plastic the clip 60 may be formed of cellulosic members. In case the inserts of FIG. 6 are preformed by being shaped from wood there is no splintering or production of fragments as in As indicated in the cross-sectional view of FIG. 2 the insert 20 has a shank 22 with a detent 23 and protruding portion 24. To retain the insert 20 securely within the aperture 15 the holder portion 13 includes projections 16 that are in locking engagement with the recesses 23 of the member 20. While two recesses 23 are shown in FIG. 2 it will be understood that a single recess can be employed and the recesses can take a wide variety of other forms.

Details of the insert 20 are shown in FIG. 3. The top 21 is proportioned to be suitable for the removal of plaque and interproximal manipulations. The insert may take a wide variety of other forms as illustrated by the brush 30 in FIG. 4.

In addition, because of the locking engagement of the insert with the handle and the extension of the hub 24 beyond the opposite entry of the aperture in the handle, the insert is easily removed as shown in FIG. 5A by pushing the hub against a flat surface. Once the insert is removed, it may be reoriented in relation to the handle by reinserting as shown in FIG. 5B. In addition the insert may be replaced when the tip 21 has worn away or is unsatisfactory because of breakage.

The handle 11 is desirably produced by injection molding of plastic. Similarly the inserts may be produced by molding and can take the form of a clip 60 as shown in FIG. 6. The clip 60 is constituted by a set of individual members 20-1 through 20-n which are individually removable from the clip 60 and insertable as shown in FIG. 5B or the converse. In addition to plastic the clip 60 may be formed of cellulosic members. In case the inserts of FIG. 6 are preformed by being shaped from wood there is no splintering or production of fragments as in the case of toothpicks used as insert. In addition the inserts are proportioned to assure a locking fit in the aperture of the associated handle.

FIG. 8 shows an alternative embodiment of the invention in which an insert 20' has a shank 22', a set of detents 23' and a protruding portion 21'. The insert 20' has a major axis and the detents 23' are provided by multiple grooves parallel to the major axis of the insert. The base of each groove is an inclined plane that diverges downwardly towards the tip 21'. FIG. 8 shows a cross section of the tip 21' as being circular.

Other aspects of the invention will occur to those of ordinary skill in the art.

What is claimed is:

1. An appliance comprising an elongated handle having opposite end portions and a rectangular aperture in one of said portions extending therethrough, which portion is angled with respect to the remainder of said handle;
    a removable insert for said aperture, said insert including a hub rectangular in cross-section and bidirectionally insertable into said aperture and having a detent therein formed by an elongated linear surface groove; and
    means in said aperture for locking into the elongated surface groove and retaining said insert therein.

2. An appliance as defined in claim 1 wherein said insert has a major axis and said detent is perpendicular to said major axis thereof.

3. An appliance as defined in claim 1 wherein said handle and said insert are of plastic.

4. An appliance as defined in claim 1 wherein said insert has a major axis and a groove perpendicular to said major axis.

5. An appliance as defined in claim 1 wherein the locking and retaining means comprises a a projection within said aperture for engaging said insert.

6. An appliance as defined in claim 1 wherein said said aperture extends through said end portion.

7. An appliance as defined in claim 6 wherein said insert is bidirectionally insertable into said aperture.

8. An appliance comprising an elongated handle having opposite end portions and an aperture in one of said portions;
    a removable insert for said aperture, said insert comprising a dental pick with a substantially rectangular hub having an elongated surface groove and a shank joined to said hub at said groove; and means in said aperture for locking into the elongated surface groove and retaining said insert thereon.

9. An appliance as defined in claim 8 wherein said insert is a dental brush.

10. An appliance as defined in claim 8 wherein said handle is of plastic.

11. An appliance as defined in claim 8 wherein said insert is of plastic.

12. An appliance as defined in claim 8 wherein the retaining means is a projection within said aperture for engaging said insert.

13. An appliance as defined in claim 8 wherein said handle is fluted by having a plurality longitudinal grooves extending therealong in order to reduce the mass of said handle and facilitate the gripping thereof.

14. An appliance as defined in claim 8 wherein said insert is rigid and projects through said aperture to permit the removal and interchangeability thereof.

15. The method of preparing a dental appliance for use, which comprises the steps of:

(a) inserting a dental contact member into a rectangular entry of an aperture in a handle for said appliance;

(b) pushing said member into said aperture until an elongated hub portion of said member engages a locking member and said hub of said member protrudes beyond an opposite entry of said aperture.

16. The method of claim 15 further including the step of applying pressure to the protrusion of said hub to expel said member from said aperture to facilitate the replacement thereof.

17. The method of claim 16 including the step of reversing the orientation of said insert with respect to said handle.

18. An appliance comprising an elongated handle having opposite end portions and an aperture in one of said portions;

a removable insert having a major axis and including a hub insertable into said aperture, said insert having a detent therein formed by multiple elongated surface grooves parallel to said major axis; and means in said aperture for locking into the elongated surface grooves and retaining said insert therein.

* * * * *